(12) United States Patent
Dugan

(10) Patent No.: US 6,509,092 B1
(45) Date of Patent: *Jan. 21, 2003

(54) HEAT BONDABLE BIODEGRADABLE FIBERS WITH ENHANCED ADHESION

(75) Inventor: Jeffrey S. Dugan, Erwin, TN (US)

(73) Assignee: Fiber Innovation Technology, Johnson City, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/286,232

(22) Filed: Apr. 5, 1999

(51) Int. Cl.[7] ................................................. D02G 3/00
(52) U.S. Cl. ........................................ 428/374; 428/364
(58) Field of Search ................................. 442/361, 364; 428/373, 374, 370, 364

(56) References Cited

U.S. PATENT DOCUMENTS

| | | |
|---|---|---|
| 3,676,242 A | 7/1972 | Prentice |
| 3,972,759 A | 8/1976 | Buntin |
| 4,041,203 A | 8/1977 | Brock et al. |
| 4,318,949 A | 3/1982 | Okamoto et al. |
| 4,622,259 A | 11/1986 | McAmish et al. |
| 4,710,187 A | 12/1987 | Boland et al. |
| 4,762,521 A | 8/1988 | Roessler et al. |
| 4,766,029 A | 8/1988 | Brock et al. |
| 4,770,656 A | 9/1988 | Proxmire et al. |
| 4,789,603 A | 12/1988 | Taniguchi et al. |
| 4,798,603 A | 1/1989 | Meyer et al. |
| 4,863,785 A | 9/1989 | Berman et al. |
| 4,950,541 A | 8/1990 | Tabor et al. |
| 5,010,145 A | 4/1991 | Ikada et al. |
| 5,057,368 A | 10/1991 | Largman et al. |
| 5,069,970 A | 12/1991 | Largman et al. |
| 5,082,899 A | 1/1992 | Sawyer et al. |
| 5,108,820 A | 4/1992 | Kaneko et al. |
| 5,126,199 A | 6/1992 | Sawyer et al. |
| 5,142,023 A | 8/1992 | Gruber et al. |
| 5,166,231 A | 11/1992 | Lee et al. |
| 5,167,765 A | 12/1992 | Nielsen et al. |
| 5,171,309 A | 12/1992 | Gallagher et al. |
| 5,185,199 A | 2/1993 | Sawyer et al. |
| 5,277,976 A | 1/1994 | Hogle et al. |
| 5,336,552 A | 8/1994 | Strack et al. |
| 5,372,885 A | 12/1994 | Tabor et al. |
| 5,382,400 A | 1/1995 | Pike et al. |
| 5,456,982 A | 10/1995 | Hansen et al. |
| 5,506,041 A | 4/1996 | Tanaka et al. |
| 5,593,778 A | 1/1997 | Kondo et al. |
| 5,698,322 A | 12/1997 | Tsai et al. |
| 5,759,569 A | 6/1998 | Hird et al. |
| 5,760,144 A | 6/1998 | Ozeki et al. |
| 5,807,973 A | 9/1998 | Gruber et al. |
| 5,814,404 A | * 9/1998 | Rutherford et al. ......... 442/361 |
| 5,916,678 A | * 6/1999 | Jackson et al. ............. 442/373 |
| 5,976,694 A | * 11/1999 | Tsai et al. ................... 428/373 |
| 6,122,537 A | * 9/2000 | Schmidt ...................... 428/373 |

* cited by examiner

Primary Examiner—Terrel Morris
Assistant Examiner—Jenna-Leigh Befumo
(74) Attorney, Agent, or Firm—Alston & Bird LLP

(57) ABSTRACT

Disclosed are multicomponent fibers which include a surface modified thermobondable non-biodegradable synthetic polymeric component and a biodegradable component. The surface modified thermobondable non-biodegradable component permits thermal bonding of the multicomponent fiber to other fibers with enhanced adhesion. The multicomponent fibers are useful in the manufacture of nonwoven structures, and in particular nonwoven structures used as a component in disposable absorbent products.

28 Claims, No Drawings

HEAT BONDABLE BIODEGRADABLE FIBERS WITH ENHANCED ADHESION

FIELD OF THE INVENTION

The present invention relates to heat bondable multicomponent fibers, and more particularly heat bondable multicomponent fibers having a biodegradable polymeric component, as well as articles incorporating the fibers as a component thereof.

BACKGROUND OF THE INVENTION

Synthetic fibers are widely used in a number of diverse applications to provide stronger, thinner, and lighter weight products. Synthetic fibers are typically heat adhesive (thermobondable) and thus are particularly attractive for the manufacture of nonwoven fabrics. Nonwoven fabrics, in turn, are widely used as components of a variety of articles, including without limitation absorbent personal care products, such as diapers, incontinence pads, feminine hygiene products, and the like; medical products, such as surgical drapes, sterile wraps, and the like; filtration devices; interlinings; wipes; furniture and bedding construction; apparel; insulation; and others.

Nonwoven fabrics can be formed entirely of synthetic fibers or a mixture of synthetic and natural fibers (such as cellulosic fibers). For example, typically disposable absorbent products include an absorbent core formed of cellulosic fluff pulp. The absorbent core can also include thermobondable synthetic fibers to thermally bind the cellulose fibers together, thereby achieving an absorbent material with improved strength. The product can also be thinner and lighter weight than traditional products.

Despite these advantages, the use of synthetic fibers in conjunction with cellulosic fluff pulp has not been without problems. For example, due to the non-polar, hydrophobic nature of conventional thermobondable fibers, the fibers can form conglomerations in the aqueous fluff pulp solution utilized during wet processing. Dry laid production of nonwovens using synthetic fibers can be difficult as well because of the lack of reactive sites on the surface of conventional thermobondable fibers. This results in a physical bonding, based on encapsulation, rather than chemical bonding. Even physical bonding is inherently difficult because of the non-polar nature of many synthetic fibers, which prevents the polymer from readily wetting out the surfaces of more polar fibers (such as cellulose fibers).

In addition, conventional synthetic fibers do not naturally degrade, thus creating problems associated with the disposal of products containing such fibers. In particular, recycling articles containing a blend of natural and conventional synthetic fibers is generally not cost effective, yet the disposal of these articles in landfills generates significant amounts of non-degradable waste. As landfills reach their capacity, the demand has increased for the incorporation of more degradable components in disposable products, as well as the design of products that can be disposed of by means other than by incorporation into solid waste disposal facilities.

To address concern over the issue of solid waste disposal, biodegradable polymers are increasingly used as a replacement for conventional synthetic polymers. Biodegradable polymers of interest include water-soluble polymers such as polyvinyl alcohol; naturally synthesized polymers such as sodium alginate and microbial polyesters; hydrolyzable aliphatic polyester and polyurethane polymers; and the like.

Synthetic biodegradable aliphatic polyesters include polyglycolide and poly(lactic)acid polymers. See, for example, U.S. Pat. Nos. 5,166,231; 5,506,041; 5,759,569; and 5,171,309.

Of particular interest is the use of lactic acid to manufacture biodegradable resin. Poly(lactic)acid (hereinafter "PLA") was initially introduced as a biodegradable polymer for medical products. U.S. Pat. Nos. 5,142,023 and 5,807,973 to Gruber et al. disclose processes by which a nonmedical grade of poly(lactic)acid may be produced and utilized in nonwoven fabrics. Examples of biodegradable fibers comprised entirely of polylactic acid polymers and/or copolymers are found in U.S. Pat. Nos. 5,010,145 and 5,760,144. See also U.S. Pat. Nos. 5,698,322 and 5,593,778 (directed bicomponent fibers which include poly(lactic acid) components).

The successful inclusion of biodegradable materials in disposable absorbent products provides several avenues by which these products may be discarded once their useful life has ended. Primarily, these articles may be easily and efficiently disposed of by composting. Alternatively, the disposable absorbent product may be easily and efficiently disposed of to a liquid sewage system wherein the disposable absorbent product is capable of being degraded.

Although biodegradable fibers are known, problems have been encountered with their use, for example, lack of control of the onset of polymer degradation. It is essential that biodegradable fiber maintain its integrity until its useful life has ended. U.S. Pat. No. 5,593,778 is directed to a core/sheath bicomponent fiber comprised entirely of poly(lactic acid), wherein the core PLA component biodegrades at a faster rate than the sheath. Although such fibers can provide some benefits, such fibers merely delay the onset of degradation and do not provide means for proactively controlling or initiating degradation of biodegradable fibers.

SUMMARY OF THE INVENTION

The present invention provides multicomponent heat adhesive or thermobondable fibers which exhibit a number of desirable, yet contradictory, properties in a single fiber structure. The fibers of the invention include a biodegradable polymeric component, thereby providing advantages in the disposal of products made with such fibers. However, in contrast to prior biodegradable fiber constructions, the fibers of the invention are structured so that initiation of degradation can be readily controlled.

In this regard, in addition to a biodegradable component, the fibers of the invention also include a thermobondable non-biodegradable polymeric component. The non-biodegradable polymeric component forms at least a portion of the exposed outer surface of the fibers, and in a preferred embodiment, completely encapsulates the biodegradable component. To control fiber degradation, the non-biodegradable polymer and biodegradable polymer can be selected so that the non-biodegradable polymer has a lower melting point (preferably at least about 10° C. lower) than the melting point of the biodegradable polymer. The fibers can accordingly be thermally treated to melt away at least a portion of the non-biodegradable polymer component to expose the biodegradable component to conditions necessary to initiate decomposition or degradation thereof. Thus the fiber degradation process can be proactively initiated, rather than merely slowed or delayed, by protecting the biodegradable component from the environment until such a time as its degradation is purposefully triggered.

In addition, because the fibers of the invention include a thermobondable polymeric component on at least a portion of the exposed surface thereof, the fibers have useful thermobonding properties, with one another and/or with different fibers. Yet in contrast to conventional thermobondable fibers, the fibers of the invention can also have useful surface properties to assist in bonding to other types of fibers (such as cellulosic fibers). As discussed above, conventional thermobondable synthetic polymeric fibers are essentially hydrophobic and lack reactive polar sites on the surface thereof. Thus it can be difficult to effectively bond such fibers with more polar fibers, such as cellulosic fibers.

In the invention, the surface properties of the thermobondable non-biodegradable polymeric component are modified using a surface active agent. In a preferred embodiment of the invention, the thermobondable non-biodegradable polymeric component includes maleic acid or maleic anhydride which adds polar groups to the surface of the fibers and imparts hydrophilic properties thereto. Biodegradable polymers typically have some polarity as compared to conventional thermoplastic polymers, such as polyester and nylon. The grafted binder thus can exhibit improved adhesion to the biodegradable component as well. The maleic acid or anhydride can be blended with or grafted onto the polymer. Thus the modified thermobondable non-biodegradable polymeric component provides both thermal bonding capability and enhanced adhesion as compared to conventional heat bondable polymers. As a result, the fibers of the invention are particularly useful in the production of nonwoven fabrics, including those used in disposable absorbent articles, such as absorbent webs formed of cellulosic fluff.

The present invention also provides fabrics formed of the multicomponent fibers of the invention, articles incorporating such fabrics as a component, processes for making the fibers and processes for controlling the degradation of articles made using the fibers.

DETAILED DESCRIPTION OF THE PREFERRED EMBODIMENTS

The present invention will be described more fully hereinafter in connection with illustrative embodiments of the invention which are given so that the present disclosure will be thorough and complete and will fully convey the scope of the invention to those skilled in the art. However, it is to be understood that this invention may be embodied in many different forms and should not be construed as being limited to the specific embodiments described and illustrated herein. Although specific terms are used in the following description, these terms are merely for purposes of illustration and are not intended to define or limit the scope of the invention.

The multicomponent fibers of the invention include at least two structured polymeric components, a thermobondable non-biodegradable synthetic polymeric component and a biodegradable polymeric component. Multicomponent fibers are formed of two or more polymeric materials. For purposes of illustration only, the present invention will generally be described in terms of a bicomponent fiber comprising two components. However, it should be understood that the scope of the present invention is meant to include fibers with two or more components.

In general, the components are arranged in substantially constantly positioned distinct zones across the cross section of the multicomponent fiber and extend continuously along the length of the multicomponent fiber. A preferred configuration is a sheath/core arrangement, wherein a first component, the sheath, substantially surrounds a second component, the core. However, other structured fiber configurations as known in the art may potentially be used, such as but not limited to, "islands-in-the-sea" arrangements, segmented cross sections and the like. Reference is made to U.S. Pat. No. 5,108,820 to Kaneko et al., U.S. Pat. No. 5,336,552 to Strack et al., and U.S. Pat. No. 5,382,400 to Pike et al. for a further discussion of multicomponent fiber constructions. The multicomponent fibers may also have unconventional shapes (such as multi-lobal) such as described in U.S. Pat. No. 5,277,976 to Hogle et al., and U.S. Pat. Nos. 5.057,368 and 5,069,970 to Largman et al.

The cross section of the multicomponent fiber is preferably circular, since the equipment typically used in the production of multicomponent synthetic fibers normally produces fibers with a substantially circular cross section. The configuration of the first and second components in a fiber of circular cross section can be either concentric or acentric, the latter configuration sometimes being known as a "modified side-by-side" or an "eccentric" multicomponent fiber.

The concentric configuration is characterized by the first component having a substantially uniform thickness, such that the second component lies approximately in the center of the fiber. In the acentric configuration, the thickness of the first component varies, and the second component therefore does not lie in the center of the fiber. In either case, the second component is substantially surrounded by the first component. However, in an acentric bicomponent fiber, a portion of the second component may be exposed, such that in practice up to about 20% of the surface of the fiber may be comprised of the second component. The first component in a fiber with an acentric configuration will nevertheless comprise the major part of the surface of the fiber, i.e., at least about 80%. Both the cross section of the fiber and the configuration of the components will depend upon the equipment which is used in the preparation of the fiber, the process conditions and the melt viscosities of the two components.

The thermobondable (or heat adhesive) non-biodegradable polymeric component advantageously has a lower melting point relative to the melting point of the biodegradable polymeric component so that the thermobondable non-biodegradable polymeric component can act as a latent adhesive. Thermal bonding is a well-known method of nonwoven fabric formation in which synthetic fibers are heated to their glass transition point or beyond, causing the fibers to soften and adhere to adjoining fibers, thereby forming a nonwoven fabric. Preferably the thermobondable non-biodegradable polymeric has a melting or softening point of at least 10° C., more preferably at least about 20° C., and most preferably at least about 25° C., less than the melting point of the biodegradable polymeric component.

In addition, the thermobondable non-biodegradable synthetic polymeric component includes a surface active agent to modify the surface properties of the polymer (i.e., to impart hydrophilicity thereto). Because the surface properties of the polymer have been modified, the fibers can exhibit improved adhesion, particularly with fibers having polar surfaces (such as cellulosic fibers). The modified surface of the thermobondable polymeric component is also thought to provide improved adhesion between the components of the multicomponent fiber itself.

Preferred polymers for use in the thermobondable non-biodegradable polymeric component are polyolefins, and in particular, long-chain, synthetic polymers of at least 85 weight percent ethylene, propylene or other olefin unit. Suitable polyolefins include polyproylene, polyethylene, polybutene, and copolymers and mixtures thereof Specific examples of polyolefins suitable for use in the thermobondable non-biodegradable component include high density polyethylene, low density polyethylene, linear low density polyethylene, poly(1-butene), polypropylene, and copolymers, terpolymers, and mixtures thereof. In addition, the thermobondable non-biodegradable polymeric component may include mixtures of polyolefins with other polymers, such as but not limited to (ethyl vinyl acetate) copolymers, (ethylene acrylic acid) copolymers, and the like. Preferably the polyolefin is a polyethylene, in particular high density polyethylene. Other suitable polymers include polystyrenes, polyurethanes, acetal resins, and copolymers, terpolymers, and mixtures thereof. In addition, polyester copolymers and polyamide copolymers may also be used.

Surface active agents suitable for the present invention include alpha, beta unsaturated carboxylic acids capable of participation in a polymer grafting reaction. In a preferred embodiment, maleic acid or maleic anhydride is grafted onto the thermobondable non-biodegradable polymer, thereby incorporating succininc acid or anhydride groups into the polymer structure.

The grafting of succininc acid or succininc anhydride groups may be done by methods described in the art which generally involve reacting maleic acid or maleic anhydride in admixture with heated polymer, generally using a peroxide or free radical initiator to accelerate the grafting. The maleic acid and maleic anhydride compounds are known to have olefin unsaturation sites conjugated to the acid groups. Fumaric acid, an isomer of maleic acid which is also conjugated, gives off water and rearranges to form maleic anhydride when heated, and is thus operable in the present invention. Grafting may be effected in the presence of oxygen, air, hydroperoxides, or other free radical initiators, or in the essential absence of these materials when the mixture of monomer and polymer is maintained under high shear and heat conditions. See, for example, U.S. Pat. Nos. 5,167,765; 5,372,885; and 4,950,541, the entire disclosure of each of which is hereby incorporated by reference.

The anhydride or acid groups of the grafted polymer generally comprise from about 0.001 to about 10 weight percent, preferably from about 0.01 to about 5 weight percent, and more preferably from 0.1 to about 1 weight percent of the grafted polymer. The grafted polymer is characterized by the presence of pendantsuccinic acid or anhydride groups along the polymer chain, as opposed to the carboxylic acid groups obtained by the bulk copolymerization of ethylene with an alpha, beta ethylenically unsaturated carboxylic acid such as acrylic acid.

The thermobondable non-biodegradable polymeric component may include the grafted polymer singly or as a component of a polymer blend. Polymers useful in such a polymer blend include the polyolefins noted above. When a blend is used, the polymer blend can contain from about 0.5 to about 99.5 weight percent of grafted polymer, preferably from about 1 to 50 weight percent grafted polymer, and more preferably from about 2 to 15 weight percent grafted polymer. See U.S. Pat. No. 5,372,885. See also U.S. Pat. Nos. 5,185,199; 5,126,199; and 5,082,899, the entire disclosure of each of which is also incorporated by reference.

The second component of the fibers of the invention includes a biodegradable polymer as known in the art. As used herein, "biodegradable" refers to a material that degrades under aerobic and/or anaerobic conditions in the presence of bacteria, fungi, algae, and other microorganisms to carbon dioxide/methane, water and biomass, although materials containing heteroatoms can also yield other products such as ammonia or sulfur dioxide. "Biomass" generally refers to the portion of the metabolized materials incorporated into the cellular structure of the organisms present or converted to humus fractions indistinguishable from material of biological origin. As a result, the biodegradable fiber, either in its initial form or after incorporation into a fabric, will begin to degrade when exposed to such microorganisms, even if such exposure occurs prior to the expiration of the fiber's useful life. Exemplary biodegradable polymers include, without limitation, polyvinyl alcohol, hydrolyzable aliphatic polyesters, hydrolyzable aliphatic polyurethanes, cis-polyisoprene, cis-polybutadiene, poly (caprolactone), hydrolyzable poly(lactic acid), poly (hydroxy alkanoates), and the like and copolymers and blends thereof. As the skilled artisan will appreciate, poly (lactic acid) is hydrolyzed before it can be consumed by microorganisms.

The biodegradable polymeric component can also be selected to provide strength or rigidity to the fiber and, thus, to nonwoven structures comprising the multicomponent fiber. Strength or rigidity of the fiber is generally achieved by selecting biodegradable component having a thermal melting temperature greater than the thermal melting temperature of the thermobondable non-biodegradable component. As a result, when the multicomponent fiber is subjected to an appropriate temperature, typically near the melting temperature of the first non-biodegradable component but less than the melting temperature of the second biodegradable component, the first component will soften while the second component will generally maintain its rigid form.

Preferably the biodegradable polymeric component comprises poly(lactic acid). In addition to biodegradability, poly(lactic acid) can impart other desirable properties to the fibers of the invention. For example, the fibers of the invention which include poly(lactic acid) as a component can exhibit improved tensile strength, as compared to fibers including polyethylene terephthalate or polyamides as a high temperature core. Further, it is believed that the fibers can exhibit improved adhesion between the polymeric components when poly(lactic acid) is used, as compared to polyethylene terephthalate and/or polyamides.

Poly(lactic acid) polymer is a biodegradable polyester polymer generally prepared by the polymerization of lactic acid. However, it will be recognized by one skilled in the art that a chemically equivalent material may also be prepared by the polymerization of lactide. Therefore, as used herein, the term "poly(lactic acid) polymer" is intended to represent the polymer that is prepared by either the polymerization of lactic acid or lactide. Reference is made to U.S. Pat. Nos. 5,698,322; 5,142,023; 5,760,144; 5,593,778; 5,807,973; and 5,010,145, the entire disclosure of each of which is hereby incorporated by reference.

Lactic acid and lactide are known to be an asymmetrical molecules, having two optical isomers referred to, respectively as the levorotatory (hereinafter referred to as "L") enantiomer and the dextrorotatory (hereinafter referred to as "D") enantiomer. As a result, by polymerizing a particular enantiomer or by using a mixture of the two enantiomers, it is possible to prepare polymers that are chemically similar yet which have widely differing properties. In particular, it has been found that by modifying the stereochemistry of a poly(lactic acid) polymer, it is possible to control the melting temperature of the polymer.

The degree of crystallinity of a PLA polymer is based on the regularity of the polymer backbone and its ability to line up with similarly shaped sections of itself or other chains. If even a relatively small amount of D-enantiomer (of either lactic acid or lactide), such as about 3 to about 4 weight percent, is copolymerized with L-enantiomer (of either lactic acid or lactide), the polymer backbone generally becomes irregularly shaped enough that it cannot line up and orient itself with other backbone segments of pure L-enantiomer polymer, thus reducing the crystallinity of the polymer, which in turn suppresses the melting point. Based on the foregoing, although a minimal amount of D-enantionmer can be tolerated, preferably the amount of D-enantiomer present in the instant invention is not such that it suppresses the melting point of the PLA component to the melting point of the first component, or to within 10° C. thereof.

Advantageously the PLA polymer also exhibits residual monomer percents effective for the second component to exhibit desirable melt strength, fiber mechanical strength, and fiber spinning properties. As used herein, "residual monomer percent" refers to the amount of lactic acid or lactide monomer that is unreacted yet which remains entrapped within the structure of the entangled PLA polymer chain. In general, if the residual monomer percent of a PLA polymer in a component is too high, the component may be difficult to process due to inconsistent processing properties caused by a large amount of monomer vapor being released during processing that cause variations in extrusion pressures. However, a minor amount of residual monomer in a PLA polymer in a component may be beneficial due to such residual monomer functioning as a plasticizer during a spinning process. Thus, the PLA polymer in the second component generally exhibits a residual monomer percent that is less than about 15 percent, preferably less than about 10 percent, and more preferably less than about 7 percent.

Each of the thermobondable non-biodegradable polymeric component and the biodegradable polymeric component can optionally include other components not adversely effecting the desired properties thereof. Exemplary materials which could be used as additional components would include, without limitation, pigments, antioxidants, stabilizers, surfactants, waxes, flow promoters, solid solvents, particulates, and other materials added to enhance processability of the first and the second components. For example, a stabilizing agent may be added to the biodegradable polymer to reduce thermal degradation which might otherwise occur during the poly(lactic) acid spinning process. The use of such stabilizing agents is disclosed in U.S. Pat. No. 5,807,973, hereby incorporated by reference. Further, additives which enhance the biodegradability of the poly(lactic)acid may optionally be included, as disclosed in U.S. Pat. No. 5,760,144, previously incorporated by reference. These and other additives can be used in conventional amounts.

The weight ratio of the thermobondable non-biodegradable polymeric component and the biodegradable polymeric component can vary. Preferably the weight ratio is in the range of about 10:90 to 90:10, more preferably from about 30:70 to about 70:30, and most preferably from about 40:60 to about 60:40.

As discussed above, the thermobondable non-biodegradable component generally provides an exposed surface on at least a portion of the multicomponent fiber, thereby permitting thermal bonding of the multicomponent fiber to other fibers (which may be the same or different from the multicomponent fiber of the present invention). Advantageously the thermobondable non-biodegradable polymeric component comprises at least about 25 percent, preferably at least about 40 percent, and more preferably at least about 60 percent, or more of the total surface area of the multicomponent fiber. In one preferred aspect of the invention, the thermobondable non-biodegradable polymeric component comprises 100 percent of the surface of the fiber (for example, the sheath of a sheath/core fiber). As a result, the multicomponent fiber is useful in the production of a wide variety of thermally bonded fibrous nonwoven structures, such as but not limited to carded webs, wet laid webs, dry laid webs, spunbonded webs, meltblown webs, and the like. While particularly useful in the production of nonwoven fabrics, the fibers of the invention can also be used to make other textile structures such as but not limited to woven and knit fabrics.

In addition, the onset of biodegradation in a multicomponent article containing a biodegradable polymer may be delayed until purposefully triggered, thereby extending the anticipated useful life of articles containing such biodegradable polymers. Therefore, in one aspect of the invention, fabric bonding occurs by simply softening the latent adhesive polymer without fully melting it, thereby leaving the latent adhesive polymer layer intact to protect the biodegradable polymer from the environment. Degradation of the fiber or article can then be initiated by a heat treatment of the fiber of the present invention, or article containing such fiber, prior to its disposal in the environment. This heat treatment is effected by exposing the fiber to sufficient energy to decrease the melt viscosity of the latent adhesive polymer so that it flows off of, or melts away from, the surface of the biodegradable polymer, thereby exposing the biodegradable polymer to the environment and triggering subsequent degradation.

In this aspect of the invention preferably the thermobondable non-biodegradable component comprises 100 percent of the surface of the fiber, thereby providing both thermal bonding properties and maximum protection to the biodegradable core. In this embodiment, a core/sheath structure is preferred. The core/sheath fiber can advantageously be incorporated into a thermally bonded nonwoven fabric, which can then be subjected to a heat treatment after the useful life of the fabric has ended.

In another aspect of this invention, the biodegradable polymer may be exposed to the environment during fabric formation. In this aspect, sufficient energy is supplied during the thermal bonding process to allow the latent adhesive polymer to flow off of the surface of the biodegradable polymer.

Methods for making multicomponent fibers are well known and need not be described here in detail. Generally, to form a multicomponent fiber, at least two polymers are extruded separately and fed into a polymer distribution system wherein the polymers are introduced into a segmented spinneret plate. The polymers follow separate paths to the fiber spinneret and are combined in a spinneret hole. The spinneret is configured so that the extrudate has the desired shape.

Following extrusion through the die, the resulting thin fluid strands, or filaments, remain in the molten state for some distance before they are solidified by cooling in a surrounding fluid medium, which may be chilled air blown through the strands. Once solidified, the filaments are taken up on a godet or another take-up surface. In a continuous filament process, the strands are taken up on a godet which draws down the thin fluid streams in proportion to the speed of the take-up godet. In the jet process, the strands are collected in a jet, such as for example, an air gun, and blown onto a take-up surface such as a roller or a moving belt to form a spunbond web. In the meltblown process, air is ejected at the surface of the spinnerette which serves to simultaneously draw down and cool the thin fluid streams as they are deposited on a take-up surface in the path of cooling air, thereby forming a fiber web. Regardless of the type of melt spinning procedure which is used, it is important that the thin fluid streams be melt drawn down in a molten state, i.e. before solidification occurs to orient the polymer molecules for good tenacity. Typical melt draw down ratios known in the art may be utilized. Where a continuous filament or staple process is employed, it may be desirable to draw the strands in the solid state with conventional drawing equipment, such as, for example, sequential godets operating at differential speeds. See, for example, U.S. Pat. No. 5,082,899.

Following drawing in the solid state, the continuous filaments may be crimped or texturized and cut into a desirable fiber length, thereby producing staple fiber. The length of the staple fibers generally ranges from about 25 to about 50 millimeters, although the fibers can be longer or shorter as desired. See, for example, U.S. Pat. No. 4,789,592 to Taniguchi et al. and U.S. Pat. No. 5,336,552 to Strack et al.

The use of poly(lactic)acid in composite fibers is especially advantageous. Poly(lactic)acid develops tensile properties which are comparable or improved in comparison to the polyester and polyamide polymers traditionally employed in the core of bicomponent binder fibers.

The multicomponent fibers of the invention can be staple fibers, continuous filaments, or meltblown fibers. In general, staple, multi-filament, and spunbond fibers formed in accordance with the present invention can have a fineness of about 0.5 to about 100 denier. Meltblown filaments can have a fineness of about 0.001 to about 10.0 denier. Monofilament fibers can have a fineness of about 50 to about 10,000 denier.

As noted above, the multicomponent fibers can be incorporated into a fabric. Fibers other than the multicomponent fibers of the invention may be present as well, including any of the various synthetic and/or natural fibers known in the art. Exemplary synthetic fibers include polyolefin, polyester, polyamide, acrylic, rayon, cellulose acetate, thermoplastic multicomponent fibers (such as conventional sheath/core fibers, for example polyethylene sheath/polyester core fibers) and the like and mixtures thereof. Exemplary natural fibers include wool, cotton, wood pulp fibers and the like and mixtures thereof. As noted above, because the fibers of the invention have modified surface properties, the fibers are particularly advantageous in combination with polar fibers, such as wood pulp fibers.

In a preferred embodiment, the multiconstituent fiber of the instant invention is incorporated into a nonwoven fabric. Staple fibers of the present invention may be formed into nonwoven webs by any means known in the art, including dry laid processes, such as carding or airlaying, as well as wet laid processes. Wet laid webs are of particular interest in the present invention, and such a process is described in U.S. Pat. Nos. 5,167,765 and 5,456,982, both hereby incorporated by reference. In addition, continuous filament may be spun directly into nonwoven webs by a spunbonding process.

Alternatively, in one embodiment of the present invention, the multicomponent fibers of the invention may be incorporated, alone or in conjunction with other fibers, into a meltblown nonwoven fabric. The technique of meltblowing is known in the art and is discussed in various patents, e.g., Buntin et al., U.S. Pat. No. 3,987,185; Buntin, U.S. Pat. No. 3,972,759; and McAmish et al., U.S. Pat. No. 4,622,259.

The nonwoven webs thus formed are typically subsequently thermally bonded to transform them into nonwoven fabrics, using any thermal bonding technique known in the art.

Nonwoven fabrics which include the multicomponent fibers of the invention as a component are particularly suited for use in disposable products. Specific examples include without limitation disposable diapers, adult incontinent products, sanitary napkins, tampons, wipes, bibs, wound dressings, and surgical capes or drapes.

The nonwoven fabrics of the invention are particularly advantageous as components of a disposable diaper. Disposable diapers typically include a liquid-permeable topsheet, a backsheet attached to the liquid-permeable topsheet, and an absorbent structure positioned between the liquid-permeable topsheet and the backsheet. The nonwoven fabrics of the invention may be incorporated into any of the components which make up the disposable absorbent product, but are preferably included in the absorbent structure. Such absorbent structures are typically multilayered, comprising at least one acquisition/distribution layer and at least one storage layer. The nonwoven fabrics of the invention are particularly useful as a component of the storage layer. Exemplary disposable absorbent products are generally described in U.S. Pat. Nos. 4,710,187; 4,762,521; 4,770,656; and 4,798,603.

The fabrics of the invention can also be used as a layer in composite fabric laminate. By combining two or more nonwoven fabrics of different types, nonwoven fabric laminates have been developed for a variety of specific end use applications. Specific examples of such fabrics are described in U.S. Pat. Nos. 3,676,242; 3,795,771; 4,041,203; 4,766,029 and 4,863,785.

The present invention will be further illustrated by the following non-limiting example.

EXAMPLE 1

Continuous melt spun core/sheath multi-filaments are produced using a bicomponent extruder. The grafted component of the bicomponent fiber consists of a high density polyethylene onto which anhydride groups have been grafted. The core component consists of polylactic acid. The ratio of grafted polyethylene to polylactic acid in the bicomponent fibers is 50/50. The polyethylene is a 30 melt index high density polyethylene commercially available as Plexar 213 from Equistar Chemical. The PLA is Heplon from Chronopol. The two components are subjected to a sheath-and-core type conventional melt spinning resulting in an "as-spun" bundle of bicomponent filaments. The filaments are subsequently drawn, thereby yielding a 3 denier multi-filament fiber.

Many modifications and other embodiments of the invention will come to mind to one skilled in the art to which this invention pertains having the benefit of the teachings presented in the foregoing descriptions. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed is:

1. A multicomponent fiber comprising:

a first component comprising a thermobondable non-biodegradable synthetic polymer and a surface active agent, said component forming an entire exposed surface of the multicomponent fiber; and a second component comprising a biodegradable polymer.

2. The fiber of claim 1, wherein said thermobondable non-biodegradable synthetic polymer is a polyolefin.

3. The fiber of claim 2, wherein said polyolefin is selected from the group consisting of polypropylene, polyethylene, polybutene, and copolymers and mixtures thereof.

4. The fiber of claim 3, wherein said polyolefin is polyethylene.

5. The fiber of claim 1, wherein said biodegradable polymer is selected from the group consisting of polyvinyl alcohol, hydrolyzable aliphatic polyesters, hydrolyzable aliphatic polyurethanes, cis-polyisoprene, cis-polybutadiene, poly(caprolactone), poly(lactic acid), and copolymers and blends thereof.

6. The fiber of claim 5, wherein said biodegradable polymer is polylactic(acid).

7. The fiber of claim 1, wherein said biodegradable polymer has a melting temperature of at least about 10° C. higher than the melting temperature of said non-biodegradable polymer.

8. The fiber of claim 1, wherein said surface active agent is maleic anhydride or maleic acid.

9. The fiber of claim 8, wherein said maleic anhydride or maleic acid is grafted onto said non-biodegradable polymer to provide succinic acid or anhydride groups on the surface of said polymer.

10. The fiber of claim 9, wherein said succinic acid and anhydride groups comprise from about 0.001 to about 10 weight percent of the grafted polymer.

11. The fiber of claim 8, wherein said maleic anhydride or maleic acid grafted polymer is blended with at least one additional polymer.

12. The fiber of claim 1, wherein said fiber is selected from the group consisting of sheath/core fibers and islands in the sea fibers.

13. The fiber of claim 1, wherein said fiber bas a circular cross-section.

14. The fiber of claim 1, wherein said fiber has a multi-lobal configuration.

15. The fiber of claim 1, wherein said fiber is selected from the group consisting of continuous filaments, staple fibers, and meltblown fibers.

16. A sheath/core bicomponent fiber, comprising:

a sheath component comprising polyethylene grafted with maleic acid or maleic anhydride; and a core component comprising poly(lactic acid).

17. A sheath/core bicomponent fiber comprising:

a sheath component comprising a thermobondable non-biodegradable synthetic polymer and a surface active agent; and a core component comprising a biodegradable polymer.

18. The fiber of claim 17, wherein said thermobondable non-biodegradable synthetic polymer is a polyolefin.

19. The fiber of claim 18, wherein said polyolefin is selected from the group consisting of polypropylene, polyethylene, polybutene, and copolymers and mixtures thereof.

20. The fiber of claim 19, wherein said polyolefin is polyethylene.

21. The fiber of claim 17, wherein said biodegradable polymer is selected from the group consisting of polyvinyl alcohol hydrolyzable aliphatic polyesters, hydrolyzable aliphatic polyurethanes, cis-polyisoprene, cis-polybutadiene, poly(caprolactone), poly(lactic acid), and copolymers and blends thereof.

22. The fiber of claim 21, wherein said biodegradable polymer is poly(lactic acid).

23. An islands in the sea multicomponent fiber comprising:

a sea component comprising a thermobondable non-biodegradable synthetic polymer and a surface active agent, said sea component forming the entire exposed surface of the multicomponent fiber; and a plurality of island components within said sea component, each comprising a biodegradable polymer.

24. The fiber of claim 23, wherein said thermobondable non-biodegradable synthetic polymer is a polyolefin.

25. The fiber of claim 24, wherein said polyolefin is selected from the group consisting of polypropylene, polyethylene, polybutene, and copolymers and mixtures thereof.

26. The fiber of claim 25, wherein said polyolefin is polyethylene.

27. The fiber of claim 23, wherein said biodegradable polymer is selected from the group consisting of polyvinyl alcohol, hydrolyzable aliphatic polyesters, hydrolyzable aliphatic polyurethanes, cis-polyisoprene, cis-polybutadiene, poly(caprolactone), poly(lactic acid), and copolymers and blends thereof.

28. The fiber of claim 27, wherein said biodegradable polymer is poly(lactic acid).

* * * * *

UNITED STATES PATENT AND TRADEMARK OFFICE
CERTIFICATE OF CORRECTION

PATENT NO. : 6,509,092 B1
DATED : January 21, 2003
INVENTOR(S) : Dugan

It is certified that error appears in the above-identified patent and that said Letters Patent is hereby corrected as shown below:

<u>Title page,</u>
Item [56], References Cited, U.S. PATENT DOCUMENTS, "4,789,603" should read -- 4,789,592 --.

<u>Column 11,</u>
Line 25, "polylactic(acid)" should read -- poly(lactic acid) --;
Line 46, "bas" should read -- has --.

Signed and Sealed this

Seventeenth Day of June, 2003

JAMES E. ROGAN
*Director of the United States Patent and Trademark Office*